(12) United States Patent
Galley et al.

(10) Patent No.: US 8,579,815 B2
(45) Date of Patent: Nov. 12, 2013

(54) DEVICE, METHOD, AND GRAPHICAL USER INTERFACE FOR SEARCHING, FILTERING AND DISPLAYING EVENT-ALIGNED INFORMATION SETS RELATED TO DIABETES

(75) Inventors: Paul J. Galley, Cumberland, IN (US); John F. Price, Mc Cordsville, IN (US)

(73) Assignee: Roche Diagnostics Operations, Inc., Indianapolis, TN (US)

( * ) Notice: Subject to any disclaimer, the term of this patent is extended or adjusted under 35 U.S.C. 154(b) by 1190 days.

(21) Appl. No.: 12/481,956

(22) Filed: Jun. 10, 2009

(65) Prior Publication Data
US 2010/0317950 A1    Dec. 16, 2010

(51) Int. Cl.
*A61B 5/00*    (2006.01)
(52) U.S. Cl.
USPC .............................. 600/365; 600/300
(58) Field of Classification Search
USPC .................. 600/309, 345–366, 300
See application file for complete search history.

(56) References Cited

U.S. PATENT DOCUMENTS

2007/0033074 A1    2/2007    Nitzan et al.
2010/0317950 A1*  12/2010   Galley et al. .................. 600/365

FOREIGN PATENT DOCUMENTS

WO    2005/093629 A2    10/2005
WO    2008/048452 A2    4/2008

OTHER PUBLICATIONS

Written Opinion of the International Search Authority, Application No. PCT/EP2010/003450, 5 pgs.
International Search Report, Application No. PCT/EP2010/003450, International Search completed Aug. 30, 2010, 6 pgs.
AACE Guidelines, American Associate of Clinical Endocrinologists Medical Guidelines for Clinical Practice for the Management of Diabetes Mellitus, Endocrine Practice, vol. 13 (Suppl 1), May/Jun. 2004, pp. 1-66.
Richard M. Bergenstal, MD., et al., Adjust to Target in Type 2 Diabetes—Comparison of a simple algorithm with carbohydrate counting for adjustment mealtime insulin glulisine, Diabetes Care, vol. 31, No. 7, Jul. 2008. pp. 1305-1310.
American Diabetes Association, Standards of Medical Care in Diabetes—2008, Diabetes Care, vol. 31, Supplemental 1, Jan. 2008, pp. 1-43.
Patricia L. Brubaker, Ph.D., Adventure Travel and Type 1 Diabetes—The complicating effects of high altitude, Diabetes Care, vol. 28, No. 10, Oct. 2005, pp. 2563-2572.

(Continued)

*Primary Examiner* — Navin Natnithithadha
(74) *Attorney, Agent, or Firm* — Dinsmore & Shohl LLP

(57) ABSTRACT

A device, method, and graphical user interface for displaying diabetes related information sets aligned by the occurrence of a particular event are disclosed. After receiving a request for an event-aligned display of diabetes related information based on an event, a search for a plurality of tagged occurrences of the event and retrieval of an information set for each of the plurality of tagged occurrences is provided. Each information set may include diabetes related information chronologically related to the tagged occurrence. The retrieved information sets is displayed on a display, wherein the retrieved information sets are shown on the display aligned by their tagged occurrences such that all diabetes related information is positioned relative the event based on its chronological relationship with the event.

18 Claims, 8 Drawing Sheets

(56) References Cited

OTHER PUBLICATIONS

Paul C. Davidson, MD, CDE, The Insulin Pump Therapy Book—Insights From the Experts, MiniMed Technologies, pp. 57-71, 1995.

Melanie Davies, MD., et al., Improvement of Glycemic Control in Subjects With Poorly Controlled Type 2 Diabetes—Comparison, Diabetes Care, vol. 28, No. 5, Jun. 2005, pp. 1282-1288.

Steven Edelman, et al., A Practical Approach for Improvement of a Basal-Prandial Insulin Therapy Regimen in Patients With Type 2 Diabetes, Osteopathic Medicine and Primary Care, Published Apr. 20, 2007, pp. 1-12.

Manju Chandran, MD., et al., Have Insulin, Will Fly: Diabetes Management During Air Travel and Time Zone Adjustment Strategies, Practical Pointers, vol. 21, No. 2, 2003—Clinical Diabetes, pp. 82-85.

Ramon Gomis, et al., Improving Metabolic Control in Sub-Optimally Controlled Subjects With Type I Diabetes: Comparison of Two Treatment Algorithms Using Insulin Glargine, ScienceDirect, Oct. 2, 2006, Elsevier Ireland Ltd, pp. 1-8.

Kjeld Hermansen, MD., et al., A 26-Week, Randomized, Parallel, Treat-To-Target Trial Comparing Insulin Determir With NPH Insulin as Add-On Therapy to Oral Glucose-Lowering Drugs in Insulin-Naive People With Type 2 Diabetes, Diabetes Care, vol. 29, No. 6, Jun. 2006, pp. 1269-1274.

Rury R. Holman, et al., Addition of Biphasic, Prandial, or Basal Insulin to Oral Therapy in Type 2 Diabetes, New England Journal of Medicine 357;17, Oct. 25, 2007, pp. 1716-1730.

Abbas E. Kitabchi, Ph.D., et al., Hyperglycemic Crises in Diabetes, Diabetes Care, vol. 27, Supplement 1, Jan. 2004, pp. S94-S102.

Howard C. Zisser, MD., et al., Restoring Euglycemia in the Basal State Using Continuous Glucose Monitoring in Subjects with Type 1 Dabetes Mellitus, Diabetes Technology & Therapeutics, vol. 9, No. 6, 2007, Mary Ann Lieber, Inc., DOI: 10.1089/dia.2007.0220, Sansum Diabetes Research Institute, Santa Barbara, California, pp. 509-515.

Laurence Kennedy, MD., et al., Impact of Active Versus Usual Algorithmic Titration of Basal Insulin and Point-of-Care Versus Laboratory Measurement of HbA1c on Glycemic Control in Patients With Type 2 Diabetes, Diabetes Care—The Glycemic Optimization with Algorithms and Labs at Point of Care (GOAL A1C) Trial, vol. 29, No. 1, Jan. 2006, pp. 1-8.

Johnson George, et al., Development and Validation of the Medication Regimen Complexity Index, The Annals of Pharmacotherapy, Sep. 2004, vol. 38, pp. 1369-1376, www.theannals.com.

Denis Raccah, et al., When Basal Insulin Therapy in Type 2 Diabetes Mellitus is Not Enough—What Next?, Diabetes/Metabolism Research and Reviews, Jan. 15, 2007, pp. 257-264, (www.interscience.wiley.com), Wiley InterScience.

Philip R. Raskin, et al., Basal Insulin of Premix Analogue Therapy in Type 2 Diabetes Patients, European Journal of Internal Medicine 18 (2007), Sep. 19, 2006, Elsevier, pp. 56-72.

Matthew C. Riddle, MD., et al., The Treat-To-Target Trial—Randomized Addition of Glargine or Human NPH Insulin to Oral Therapy of Type 2 Diabetic Patients, Diabetes care, vol. 26, No. 11, Nov. 2003, pp. 3080-3086.

Guidelines—for Sick Day Management for People with Diabetes, Established 1981, ADEA, pp. 1-6, 2006, Australia.

Symlin (pramlintide acetate) injection Rx only—Label, 812004-EE-RL01, NDA 21-332, pp. 1-47, Amylin Pharmaceuticals, Inc., http://www.symlin.com, 2005.

Rachel Gifford, et al., Diabetes Care When You're Sick, Diabetes Forecast, Feb. 2005, pp. 44, 46-50.

Accu-Chek Camit Pro, Diabetes Management Software, User's Manual, Version 2.4 Addendum and Version 2.1 User's Manual, Catalog No. 03576680001, pp. 1-220, Jun. 27, 2005.

\* cited by examiner

DEVICE, METHOD, AND GRAPHICAL USER INTERFACE FOR SEARCHING, FILTERING AND DISPLAYING EVENT-ALIGNED INFORMATION SETS RELATED TO DIABETES

TECHNICAL FIELD

The present invention relates generally to displaying diabetes related information, and in particular to a graphical user interface and device displaying diabetes related information sets aligned by the occurrence of a particular event and a method thereof.

BACKGROUND

For people with diabetes, regular testing of their blood glucose level can be an important part of diabetes management. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood. The portable handheld glucose meter then measures concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor blood glucose in one's home, healthcare facility or other location, for example, by persons having diabetes or by a healthcare professional.

Health care professionals and patients are taught to look for abnormal glucose patterns related to medications, diet and activity and identify the causes and successful resolution of cases of hypoglycemia or extended hyperglycemia. To enable this process, patients may either manually or automatically (via a portable handheld glucose meter or alternative electronic device) record and track diabetes related information. These logs, taken over an extended period of time, allow patients and professionals alike to look back at and analyze glucose information. Traditionally, log books chronologically relate information to a time in the day by recording when the information were taken. This can allow for patients with routine and predictable habits to overlay information from multiple days and observe the variation in glucose levels around a routine event. For example, one may overlay a weeks worth of data taken between breakfast and two hours after breakfast to examine the role that meal plays on an individual.

While such practices allow for the study of routine habitual undertakings, it is ineffective for analyzing sporadic events that occur infrequently or irregularly. Overlaying measurement sets for repetitious time frames fails to account for events such as exercise, illness, stress, snacking, hypoglycemia or hyperglycemia that can arise at anytime and for any duration. Thus, it may be desirable to provide an alternative method of displaying diabetic information to account for irregular or infrequent events.

SUMMARY

In one embodiment, a method for displaying diabetes related information includes receiving a request for an event-aligned display of diabetes related information based on an event. The method further includes searching for a plurality of tagged occurrences of the event and retrieving an information set for each of the plurality of tagged occurrences. Each information set includes diabetes related information chronologically related to the tagged occurrence. The method may then include displaying the retrieved information sets on a display, wherein the retrieved information sets are shown on the display aligned by their tagged occurrences such that all diabetes related information is positioned relative the event based on its chronological relationship with the event.

In another embodiment, a device for searching, filtering and displaying event-aligned information sets related to diabetes is disclosed. The device includes a display, an input terminal for making a request for an event-aligned display of diabetes related information based on an event, and memory for storing the diabetes related information and instructions. The device further includes a processor in communication with the memory and operable to execute the instructions, the instructions causing the processor to search for a plurality of tagged occurrences of the event and retrieve an information set for each of the tagged occurrences based on the request, the information sets include diabetes related information chronologically related to the tagged occurrences, and to display on the display such retrieved information sets wherein the retrieved information sets are aligned by their tagged occurrences such that all diabetes related information is positioned relative the event based on its chronological relationship with the event.

In still yet another embodiment, a method allows for displaying diabetes related information. The method includes determining an event and a time frame for analysis, requesting an event-aligned display of diabetes related information based on the event and the time frame via an input device of a device having a display, a processor and memory, wherein the event is entered via the input device, the processor searches the memory for a plurality of tagged occurrences of the event within the time frame, retrieves an information set for each of the plurality of tagged occurrences, each information set including diabetes related information chronologically related to the tagged occurrence, and displays the retrieved information sets on the display, the information sets being aligned by their tagged occurrences such that all diabetes related information is positioned relative the event based on their chronological relationship with the event.

In another embodiment, a graphical user interface (GUI) for displaying event-aligned information sets on a device with a display is disclosed. The GUI comprises a graph area; a date range list box; wherein in response to processing of the device on a time frame listed in the date range list box and a request for an event-aligned display of diabetes related information based on an event, information sets are displayed in the graph area aligned by tagged occurrences of the event within the time frame such that all diabetes related information are positioned relative the event based on their chronological relationship with the event.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

Embodiments of the present invention are directed to searching, filtering and displaying event-aligned information sets related to diabetes. Patients may wear devices that periodically monitor for diabetes related measurements, and may input test results or other diabetes related information into a common database. Despite the method of collecting information, all information may be identified by the time it was taken. Operators may then search through the information database to identify information sets chronologically related to specific events so that a plurality of information sets related to a common type of event may be compared and analyzed.

Figure 1:
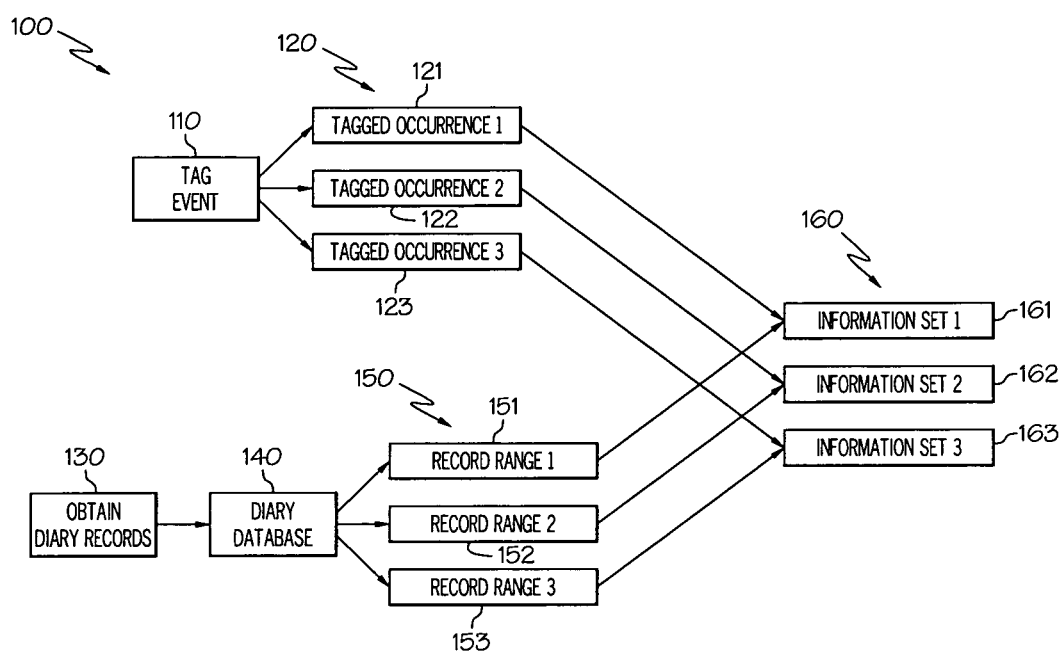
FIG. 1 depicts a logistical flowchart of obtaining information sets correlated with event occurrences according to one or more embodiments shown or described herein.

Referring to FIG. 1, a logistical flowchart 100 is depicted showing events 110 from which tagged occurrences 120 are obtained as well as obtaining diary records 130 in a diary database 140 from which record ranges 150 are correlated with the tagged occurrences 120 to provide information sets 160. A patient may obtain diary records 130 comprising diabetes related information from their blood or by recording activity information (such as a food record, sport type or medication dosages) that may be relevant to the diagnosis, control or treatment of diabetes. For example, such diary records may include diabetes related information such as glucose levels, glycemic index values, or food, activity or medication information. The diary records may be taken periodically through manual or automatic testing, continuously through a continuous blood glucose meter, sporadically from hospital visits or by any other frequency. The diary records may then be collected and stored in a diary database 140 and may be identified by the time in which they were obtained. Through identifying the time in which diary records were obtained, groups of information or measurements (indicated as record ranges 150) taken during specified time frames may be obtained from the diary database 140. For example, a record range 150 may comprise all blood glucose information obtained during a defined four, five or six hour period, or with some events a series of one or two days before and after the event. Specifically, record ranges 150 may allow for the investigation of the change in diabetes related information such as blood glucose or medication levels during a given time frame.

The occurrence of various events 110 are correlated with obtained diary records 130 to investigate the change in diary records (such as food, activity or medication), during or after an event occurrence. An event 110 may mean any activity or condition that may repeat itself periodically or sporadically. For example, events 110 may include, but not be limited to, hypoglycemia, exercise, illness, stress, menstrual state, meals, test meals, ketosis, therapeutic changes, hyperglycemia, new exercise or the start of a sport season. In order to correlate events 110 with diary records 130, the events are identified or "tagged" either manually or automatically to define a plurality of tagged occurrences 120. The tagging of events 110 may occur in a variety of fashions. For example, where the event is of the type that the patient voluntarily engages in an activity (such as exercise or eating), the patient may manually tag the event themselves. In one embodiment, a patient may enter the event 110 (similar to adding an appointment to a calendar) on their blood glucose monitor, personal digital assistant, laptop, desktop or the like so long as it may be correlated with the diary database 140 either simultaneously or at a later time. In another embodiment, such as when a patient wears a continuous glucose meter, the patient may select the event 110 from a drop-down type menu on the display of the continuous blood glucose meter to enter a time-stamp of the event occurrence. In yet another embodiment, a blood glucose meter may comprise a plurality of buttons each relating to a specific event wherein the patient may select the appropriate event when it occurs. Any other form of manually tagging of events 110 may otherwise be employed so long as the tagged occurrences 120 may be chronologically compared to the diary database 140, and in no means are these exemplary embodiments meant to be exhaustive.

In the alternative, events 110 may automatically be defined based on external conditions or from obtained diary records such as obtained glucose measurements. For example, a blood glucose meter may comprise a condition detector for detecting external conditions such as movement or temperature. Where the condition detector detects an event, it may automatically tag the event based on its occurrence. For example, a blood glucose meter may comprise an accelerometer to detect extreme movement such as running or other forms for exercise or physical activity. A program running on the blood glucose meter may thereby automatically tag an event of "physical activity" when a signal from the accelerometer indicates such extreme movement, such as for example, the program determines that the signal from the accelerometer exceeds a pre-determined acceleration level and/or which continues longer than a predetermined time. As used herein, a program is a set of instructions that when executed by a processor causes the processor to perform the stated process or processes.

In another embodiment, events 110 may be based on the examination of obtained measurements recorded in the diary database. For example, a program may automatically tag an event of hypoglycemia or hyperglycemia whenever an individual's blood glucose falls below or rises above a predetermined value such as 70 mg/dl. Other events for detection may include hyperglycemia or other conditions that may be obtained from the analysis of blood measurements. Such automatic tagging may occur dynamically as the measurements are obtained, or may occur at a later time. For example, a program may scan the diary database 140 after a plurality of measurements were obtained to determine when events of hypoglycemia or hyperglycemia occurred and tag events accordingly. In an alternative embodiment, tagged occurrences 120 may be tagged with additional categorical information such that a variety of search requests would find the same event. For example, a search request for "meals" may produce any tagged occurrences of breakfasts, lunches or dinners. Such categorical expansion may be added manually or automatically when events are tagged.

Still referring to FIG. 1, a plurality of tagged occurrences 121,122,123 may therefore be correlated with a plurality of record ranges 151,152,153 to form a plurality of information sets 161,162,163. In essence, each information set 160 comprises the information (e.g., measurements) obtained within a chronological relationship (for example, within three hours) of the event occurrence. The amount of information or the number of measurements, within each information set 160 and the chronological relationship may be adjustable or otherwise vary as will become appreciated below.

Figure 2:
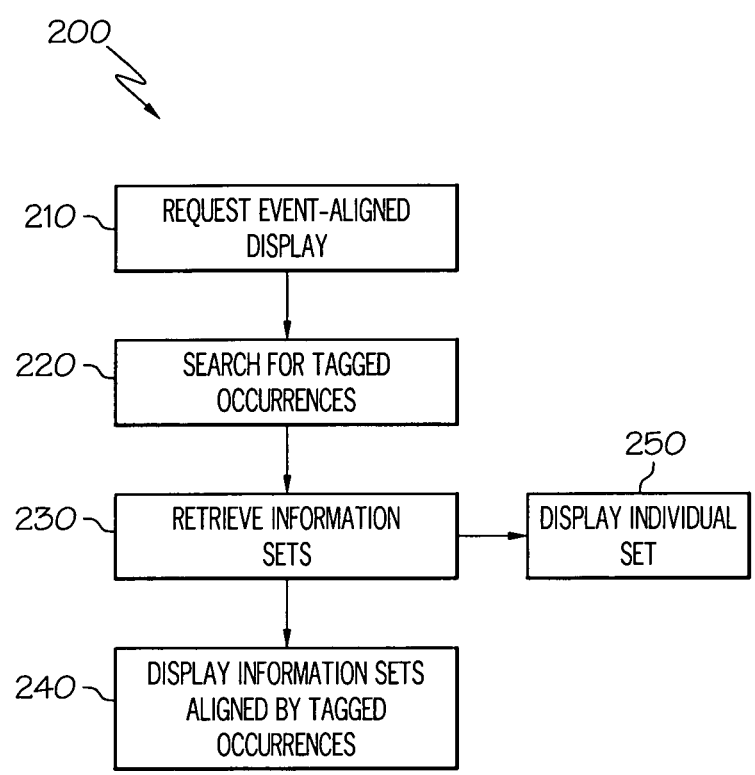
FIG. 2 depicts a logistical flowchart for displaying event-aligned information sets according to one or more embodiments shown or described herein.

Referring now to FIGS. 1 and 2, an exemplary method 200 for displaying event-aligned information sets is shown. The method 200 may first comprise receiving a search request in step 210 from an operator for an event-aligned display of a plurality of information sets 160. The search request in step 210 may be made from a patient, a physician, a laboratory or any other person or entity that may desire to review information relevant to diabetes. The search request in step 210 may be the mere identification of the event to be examined, or may include further parameters or variables as the operator sees fit such as the ability to exclude certain results or information sets 160. For example, an operator may submit the search request in step 210 for an event-aligned display of glucose levels within a chronological window of workout sessions. In another example, the operator may specify in step 210 the boundaries of the chronological window (i.e., how many hours before or after the workout to include), how many workout sessions should be retrieved, how far back in time the search should go, or combinations thereof. The search request in step 210 may be entered on the blood measurement device itself or may be entered on another computing platform with access to the diary database 140. For example, in one embodiment, the search request in step 210 may be selected through entering an event type from a drop down list. In another embodiment, the operator may be able to search for event types and then select a specific event type from the applicable results. In yet another embodiment, the an operator may be able to progress through a survey-style type of questionnaire where each response limits the amount of events to select from. For example, the operator may first select physical activity and further select outdoor sports. A list of outdoor sports may then be displayed for an operator to select from so that the search request in step 210 may be formed. Other methods may alternatively exist that allow for the entering of an event to develop the search request in step 210.

Once a search request in step 210 is made, a search for tagged occurrences of the event is performed in step 220. The search in step 220 may be performed in any variety of methods operable to retrieve a plurality of tagged occurrences 120 and may be influenced by the actual search request received in step 210. In one embodiment, the search may analyze all tagged events starting with the most recent in time and proceed backwards finding all those events matching the search request. For example, where the search request was for "eating," the search will proceed through all events while filtering out non-matching events such as "exercise" and "illness." The search in step 220 may proceed until it finds a specified number of positive results, until it reaches a specified point in time or until it reaches the end of all tagged events. Furthermore, the search in step 220 may comprise searching an exact word or may alternatively comprise selecting a categorical title from a list of options that may return results having different titles but relating to a common category (for example, returning "soccer practice" and "weight lifting" for the categorical title of "physical activity"). Any other suitable method for searching may alternatively be employed in step 220 where it capably identifies tagged occurrences 120 relevant to the search request received in step 210.

After the search for tagged occurrences in step 220, information sets 160 are obtained based on record ranges 150 in step 230. Specifically, for each tagged occurrence 121,122, 123 a record range 151,152,153 is obtained for the given time frame. For example, if tagged occurrence 1 (see tagged occurrence 121 in FIG. 1) occurred on a given day at 3 pm, all information such as glucose measurements or food records obtained for that same day between 1 pm and 5 pm may be retrieved as record range 1 (see record range 151 in FIG. 1). Depending on the default parameters, or the parameters of the search request in step 210, the actual chronological window may be manipulated or adjusted. Tagged occurrence 1 (see tagged occurrence 121 in FIG. 1) may be combined with record range 1 (see record range 151 in FIG. 1) to form information set 1 (see information set 161 in FIG. 1). Information set 1 may thereby allow for an operator to analyze obtained diary records surrounding an event based on their chronological relationships. The retrieving of information sets in step 230 may continue until a record range is matched with each tagged occurrence produced from the search in step 220 or until it is determined that no such record range exists.

Once information sets are retrieved, they may be displayed in step 240 wherein each information set is aligned by the tagged occurrence. That is, for example, diabetes related information in record range 1 taken one hour after tagged occurrence 1 will be aligned with diabetes related information in record range 2 taken one hour after tagged occurrence 2. Thus, despite tagged occurrences 120 potentially occurring at irregular periods throughout the days, their relevant record ranges 150 can be aligned and compared. In one embodiment, various parts of the method 200 may be repeated or performed in a different order to expand upon or adjust the display of information sets aligned by tagged occurrences. For example, once an initial search request is performed and the results are displayed, the operator may modify the search by, for example, manipulating the dates to be searched or expanding the amount of results to be retrieved. Accordingly, the exemplary method 200 may repeat itself in part or in its entirety to fulfill the modified search request so long as it results in displaying information sets aligned by tagged occurrences. Alternatively, once information sets are retrieved in step 230, an individual information set 250 may be displayed in step 250. This may allow for a more detailed examination of an individual information set as will become appreciated later herein.

Figure 3:
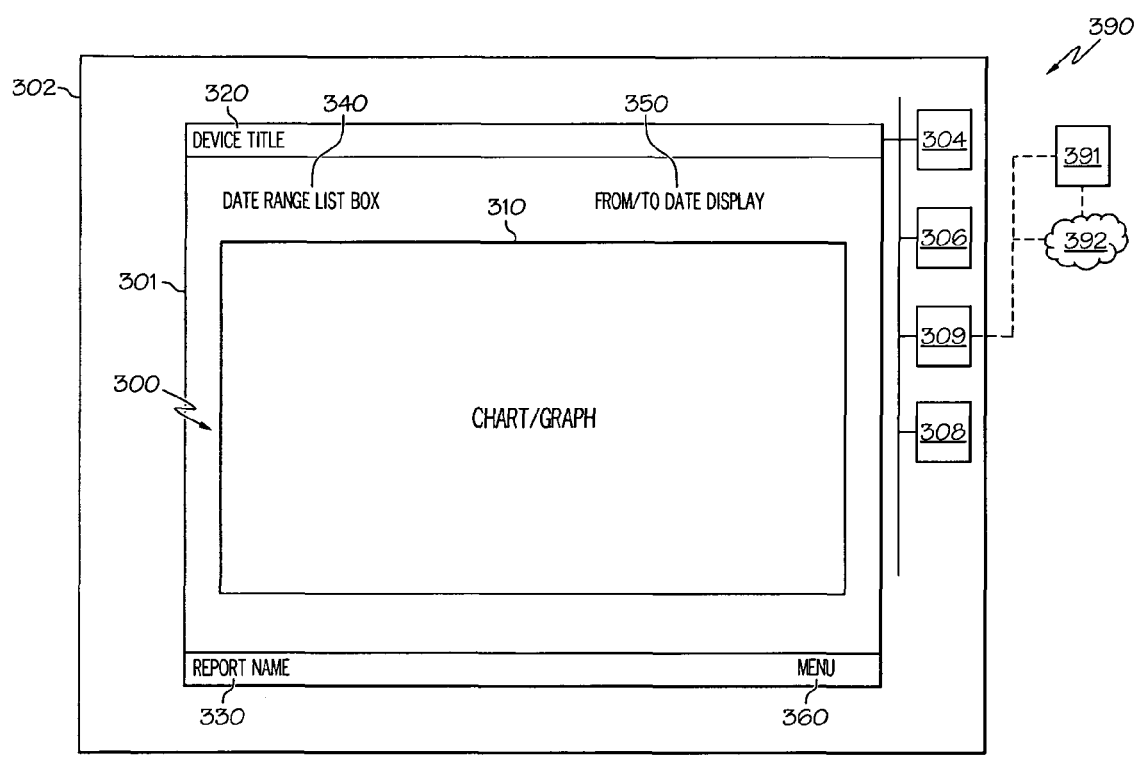
FIG. 3 depicts an exemplary graphical user interface (GUI) display according to one or more embodiments shown or described herein.

Referring now to FIG. 3, an exemplary graphical user interface (GUI) 300 for displaying event-aligned information sets is shown. The GUI 300 may be integrated with a device 302 or may comprise a generic visual format used as a template for computer based programs. For example, in one embodiment, a device 302 may comprise the GUI 300 provided on a display 301, a processor 304, memory 306 and one or more input terminals 308, 309 operably connected together and powered by a suitable power supply (not shown). The processor 304 may process information such as search requests or searching/filtering algorithms. The memory 306 may be operable to store the programs mentioned earlier and in sections hereafter, program instructions which cause the processor 304 to perform the steps of method 100, and information such as the diary database 140, tagged occurrences 120, previous search requests or operator preferences. The input terminal 308 may comprise any mechanism for inputting data, operator feedback or other information for routine handling by the processor of the device. For example, in one embodiment the device 302 may comprise an input terminal for receiving information and another input terminal for operator communication such as a keyboard or a touch screen. In addition, examples of routine handling may include the processor 304 storing input received via the input terminal 308 into the memory 306, retrieving information from the memory 306 based on input received via the input terminal 308, like a request for an event, transforming such retrieved information into a different form or state, and/or displaying the transformed information via the GUI 300 on the display 301. In another embodiment, the device 302 may be part of an information system, generally indicated by symbol 390, such as, for example, where a server 391 provides instructions and stores information such as the diary database 140. In such an embodiment, the server 391 may communicate either directly or over a network 392, e.g., LAN, WAN, Internet, and the like, with the device 302 via communications hardware 309 enabling wired and/or wireless communications therewith. As the communication hardware 309, server 391, and network 392 are conventional and well understood by those skilled in the art, no further discussion is provided.

In one particular embodiment, the processor 304 is in communication with the memory 306 (and/or server 391) and operable to execute instructions stored therein. The instructions when executed by the processor 304 cause the processor to search for a plurality of tagged occurrences 120 of an event 110 received via a request inputted via the input terminal 308, and to retrieve an information set 160 for each of the tagged occurrences based on the request. In one embodiment, the information sets 160 comprise diabetes related information chronologically related to the tagged occurrences 120. The instructions further cause the processor 304 to format and display on the display 301 the retrieved information sets 160, wherein the retrieved information sets are aligned by their tagged occurrences 120. In one embodiment, the format is such that all diabetes related information is positioned relative to the event 110 based on its chronological relationship with the event.

In other embodiments, the device 302 which employs such programs and the GUI 300 mentioned herein may be, but not be limited to, the blood glucose meter mentioned in earlier sections, a personal digital assistant (PDAs), a cell phone, a smart phone, an electronic logbook or any other computing device such as a laptop, a desktop or web-based computing platform. In still another embodiment, the GUI 300 may be accessed through a program capable of being installed on or accessed by various computers, hand held devices or the like. Furthermore, the GUI 300 may comprise a full color screen, a black and white screen, a monochromatic screen or any other color variation. The display 301 may comprise a liquid crystal display (LCD), a plasma display, a cathode ray tube (CRT), a projection display or any alternative technology operable to display information sets 160 for an operator.

Still referring to FIG. 3, the GUI 300 may generally comprise various features such as, but not limited to a graph area 310, a device title 320, a report name 330, a date range list box 340, a from/to date display 350, a menu 360 or any combination thereof. Additional features for displaying relevant information pertinent to the operator may further be provided throughout the GUI 300. Furthermore, each display feature may comprise a graphical area about the GUI 300 or may be positioned proximate reference indicia adjacent the GUI 300 for aiding in the interpretation of display information. Display features may additionally be customizable in their overall size, position, appearance or existence as an operator sees fit.

The graph area 310 may be used for visualizing information sets as discussed above. For example, a plurality of information sets may be overlaid atop one another (and aligned by tagged occurrences) in the graph area 310. Depending on the type of display, the graph area 310 may be full color, black and white or any variation. In one embodiment, the operator may selectively manipulate the visual appearance settings of the graph area 310 such as, for example, the brightness, contrast or height-to-width ratio. The device title 320 may display information about the display such as the make or model of the glucose meter used to take information or, if distinct, the device presently used to display the information. The report name 330 may display information pertaining to the displayed information sets or search request. For example, where the operator can save a search request, the report name 330 may display its title such as the date the search request was made. The date range list box 340 may display various date ranges the operator may select for display. For example, the date range list box 340 may comprise a drop down list from which the operator may selectively pick various date ranges. Likewise, the from/to date display 350 may display information regarding the date parameters of the search or the date parameters of the displayed information sets. A menu 360 feature may also be provided about the GUI 300 providing access to further options for display manipulation.

Figure 4:
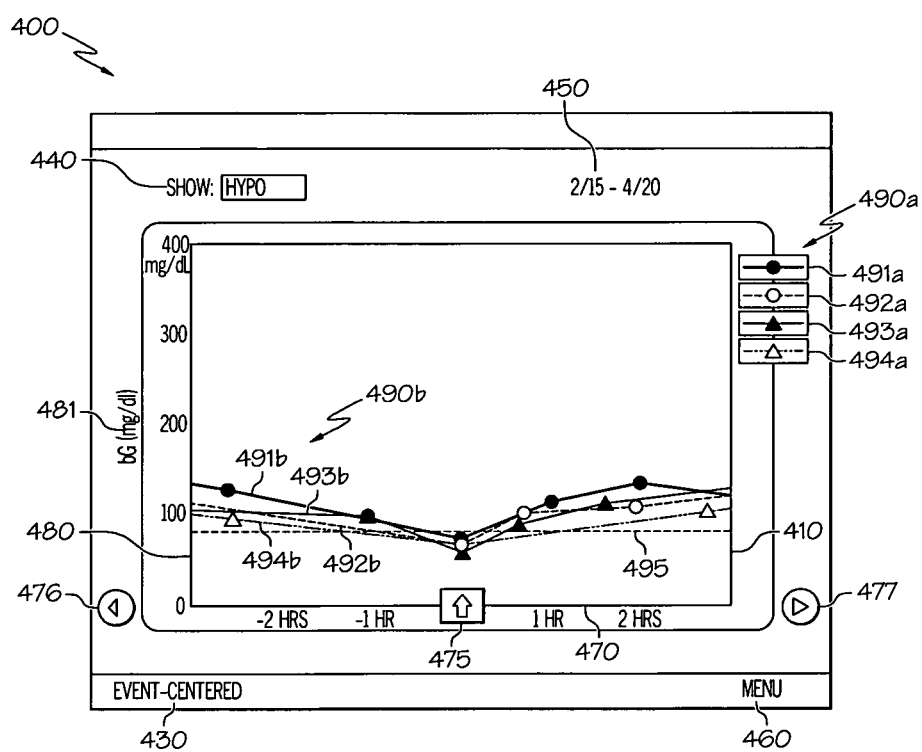
FIG. 4 depicts a GUI display visualizing event-aligned information sets according to one or more embodiments shown or described herein.

Referring now to FIG. 4, an exemplary graphical user interface (GUI) 400 is shown comprising multiple information sets 490b overlaid on a common graph 410 and aligned by their tagged occurrences at an event indicator 475. The graph area 410 comprises an independent axis 470 (the x-axis) and a dependant axis 480 (the y-axis) indicating the chronological time lapse and blood glucose level respectively. The independent axis 470 further comprises the event indicator 475 that represents when the tagged event occurred and the amount of time lapsed either before or after the event. As discussed above, events may include hypoglycemia, exercise, illness, stress, menstrual state, meals, test meals, ketosis, therapeutic changes, hyperglycemia, new exercise or the start of a sport season and may be either manually or automatically generated. The dependent axis 480 further comprises a label 481 indicating the data shown. Specific to FIG. 4, the dependant axis 480 shows blood glucose (or bG); however, alternative measurements may be shown as discussed above such as ingested medication amounts such as the glycemic index (GI). The GUI 400 further comprises a title 430 and additional features dispersed about the graph area 410.

Within the graph area 410, four information sets 490b are shown based on events of hypoglycemia. Specifically, as indicated by reference line 495, all four information sets 490b were produced from tagged events of hypoglycemia, or where the bG level dropped below about 70 mg/dl, and aligned about the event indicator 475. The information sets 490*b* comprise information within ±3 hours of the tagged event and are referenced by the legend 490*a*. In one embodiment, each individual information set 490*b* may be selectively removed from the graph area 410. For example, where the display providing the GUI 400 is a touch screen display, an operator may selectively touch an information set in the legend (see measurement sets 491*a*, 492*a*, 493*a*, 494*a*) to remove its corresponding information set in the graph area (see measurement sets 491*b*, 492*b*, 493*b*, 494*b*). Furthermore, forward arrow 477 and backwards arrow 476 may be selected to cycle through individual information sets. Alternatively, the forward arrow 477 and backwards arrow 476 may be selected to advance or retreat the display in time. Depending on the searching method employed, the obtained measurements from the diary records may already be obtained for display, or a modified search may be required to obtain the desired information. The from/to date display 450 may alternatively be used to adjust which information sets 490*b* are displayed or how to modify the initial search. Other alternative display manipulation features may include the ability to change the type of event shown 440 or adjust other visual features within the menu 460.

Figure 5A:
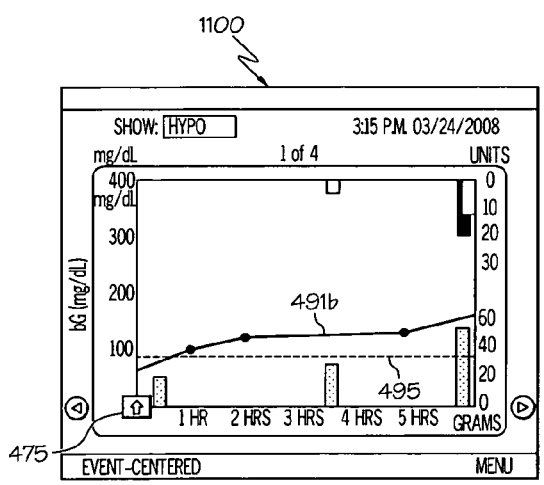
FIG. 5A depicts a GUI display visualizing an event-referenced information set with a plus-six hour window according to one or more embodiments shown or described herein.
Figure 5B:
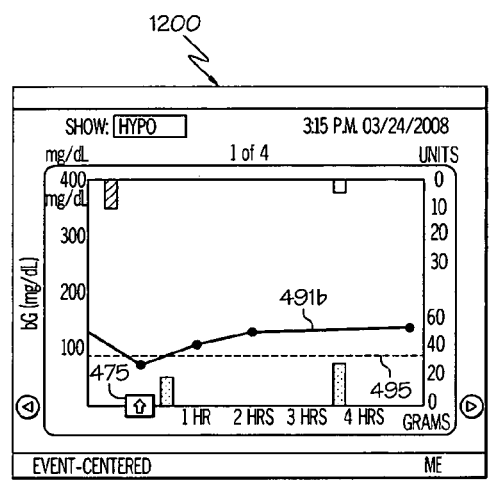
FIG. 5B depicts a GUI display visualizing an event-referenced information set with a minus-one to a plus-five hour window according to one or more embodiments shown or described herein.
Figure 5C:
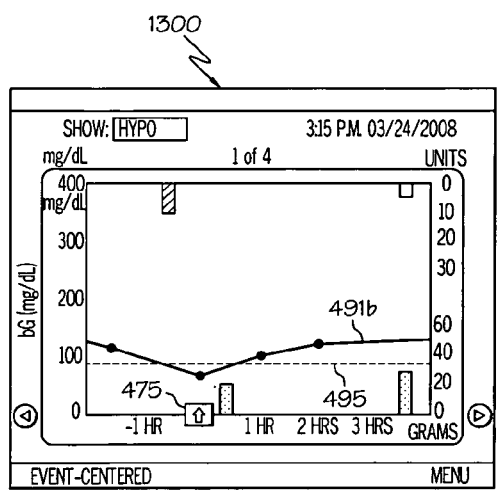
FIG. 5C depicts a GUI display visualizing an event-referenced information set with a minus-two to a plus-four hour window according to one or more embodiments shown or described herein.
Figure 5D:
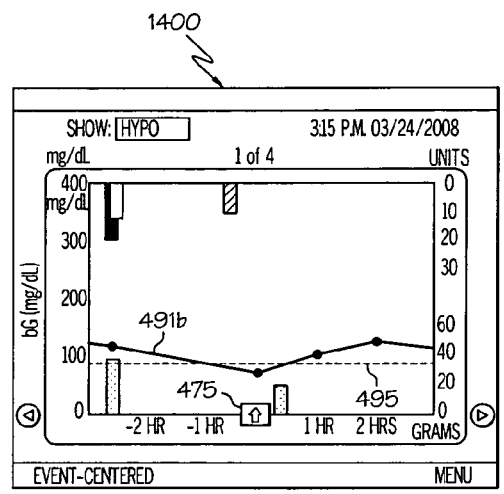
FIG. 5D depicts a GUI display visualizing an event-referenced information set with a minus-three to a plus-three hour window according to one or more embodiments shown or described herein.
Figure 5E:
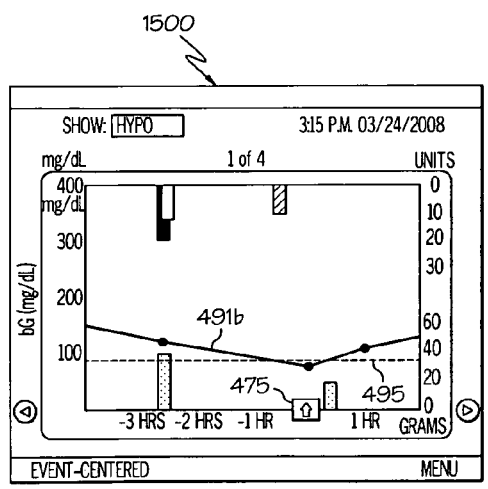
FIG. 5E depicts a GUI display visualizing an event-referenced information set with a minus-four to a plus-two hour window according to one or more embodiments shown or described herein.
Figure 5F:
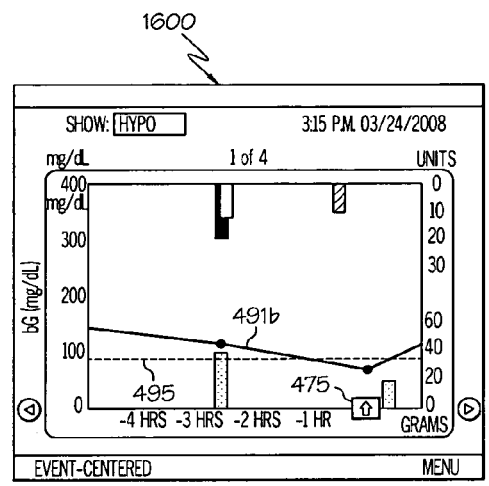
FIG. 5F depicts a GUI display visualizing an event-referenced information set with a minus-five to a plus-one hour window according to one or more embodiments shown or described herein.
Figure 5G:
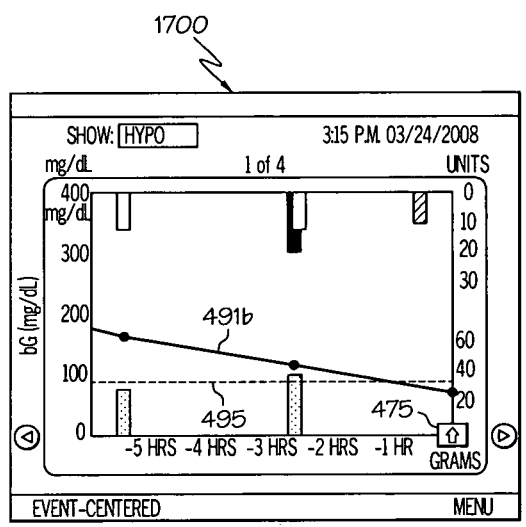
FIG. 5G depicts a GUI display visualizing an event-referenced information set with a minus-six hour window according to one or more embodiments shown or described herein.

In one embodiment, an operator may wish to focus in on a single information set or otherwise display additional related information on the same GUI display. Referring to FIGS. 5A-5G, a series of GUI displays 1100-1700 are shown displaying the first four information sets 491*b* with the event indicator 475 and the reference line 495 wherein the display area is progressively scrolled backwards in time to see additional information relating to the tagged event. Specifically, FIG. 5A shows the information set 491*b* with all other information sets removed from the display area. Additional obtained information may also be displayed about the graph area and referenced by values on the right-hand axis. Initially, as seen in FIG. 5A, obtained diary records for the time frame of the event plus six hours are shown. The event then progresses from left-to-right in one hour increments until the information is shown for the event minus six hours (see FIG. 5G). This may allow for an operator to better focus their analysis on an individual information set.

It should now be understood that diabetes related information sets may be aligned by event occurrences for the analysis of information surrounding occurrences of sporadic or inconsistent events. The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A method for displaying diabetes related information comprising:
    tagging at least manually with user defined identifying information in a diary database occurrences of various events, which repeat at least sporadically, to correlate the tagged occurrences of the various events with diary records such that a plurality of tagged occurrences are defined;
    receiving by a processor, via an input terminal, a request for an event-aligned display of diabetes related information based on an event from the various events, the request being at least an exact word or categorical title;
    searching, via the processor, the plurality of tagged occurrences in the dairy database for tagged occurrences of the event matching the request;
    retrieving, via the processor, an information set for each of the plurality of tagged occurrences from the diary database that match the request, wherein each information set comprises diabetes related information chronologically related to the tagged occurrence; and
    displaying the retrieved information sets on a display, wherein the retrieved information sets are shown by the processor on the display aligned by their tagged occurrences such that all diabetes related information are positioned relative the event based on their chronological relationship with the event.

2. The method of claim 1 wherein tagged occurrences comprise exercise, illness, stress, menstrual state, meal, ketosis, and/or therapeutic changes.

3. The method of claim 1, further comprising tagging occurrences automatically based on the diabetes related information or external conditions.

4. The method of claim 3 wherein the diabetes related information comprises glucose levels and events of hypoglycemia or hyperglycemia are automatically tagged when a glucose level drops below or rises above a threshold value.

5. The method of claim 1 wherein each information set may be selectively removed from the display.

6. The method of claim 1 wherein searching for a plurality of tagged occurrences comprises searching backwards in time from a most recent tagged occurrence.

7. The method of claim 6 wherein the plurality of tagged occurrences comprises between four and seven tagged occurrences.

8. The method of claim 1 wherein the diabetes related information comprises glucose levels.

9. The method of claim 8 wherein the glucose levels are obtained via a continuous blood glucose meter.

10. The method of claim 1 wherein displaying the information sets is performed on a touch screen display providing a graphical user interface which also receives the request.

11. The method of claim 10 wherein the display may be scrolled forward or backwards in time.

12. The method of claim 10 wherein each of the plurality of information sets may selectively be displayed through engaging the touch screen display.

13. The method of claim 1 further comprising tagging the tagged occurrences with additional categorical information such that a variety of search requests would find the same event.

14. A device for searching, filtering and displaying event-aligned information sets related to diabetes, comprising:
    a display;
    an input terminal for making a request for an event-aligned display of diabetes related information based on an event, the request being at least an exact word or categorical title;
    memory for storing the diabetes related information and instructions;
    a processor in communication with the memory and operable to execute the instructions, the instructions causing the processor:
    to tag in memory occurrences of various events, which repeat at least sporadically, with at least manually entered user defined identifying information to correlate the tagged occurrences of the various events with diary records contained in memory such that a plurality of tagged occurrences are defined, to receive via the input device the request for the event-aligned display of diabetes related information based on the event from the various events, to search the plurality of tagged occurrences for tagged occurrences of the event matching the request and retrieve an information set for each of the tagged occurrences that match the search request, the information sets comprising diabetes related information chronologically related to the tagged occurrences, and to display on the display such retrieved information sets wherein the retrieved information sets are aligned by their tagged occurrences such that all diabetes related information is positioned relative the event based on its chronological relationship with the event.

15. The device of claim 14 wherein the display comprises a touch screen display.

16. The device of claim 14 further comprising communications hardware enabling communications with a server having a diary database, wherein the device stores the diabetes related information contained in the memory to the diary database of the server through said communications.

17. The device of claim 14 wherein the device is a blood glucose meter.

18. The device of claim 14 wherein the instructions further causes the processor to tag the tagged occurrences with additional categorical information such that a variety of search requests would find the same event.

* * * * *